United States Patent [19]

Kanayama et al.

[11] Patent Number: 4,978,810
[45] Date of Patent: Dec. 18, 1990

[54] POLYALKENYLPHENOL COMPOUND

[75] Inventors: Kaoru Kanayama; Shuji Ichikawa, both of Ibaraki, Japan

[73] Assignee: Mitsubishi Petrochemical Co., Ltd., Tokyo, Japan

[21] Appl. No.: 408,387

[22] Filed: Sep. 18, 1989

[30] Foreign Application Priority Data

Sep. 28, 1988 [JP] Japan .................. 63-242959

[51] Int. Cl.$^5$ ................ C07C 39/367; C07C 39/373; C07C 39/40
[52] U.S. Cl. .................. 568/720; 568/717; 568/718; 568/719
[58] Field of Search ............... 568/718, 720, 717, 719

[56] References Cited

U.S. PATENT DOCUMENTS 4,415,724 11/1983 Mark et al. .................. 568/720

FOREIGN PATENT DOCUMENTS 1251634 11/1986 Japan .................. 568/720
2045546 2/1987 Japan .................. 568/720

Primary Examiner—Werren B. Lone
Attorney, Agent, or Firm—Oblon, Spivak, McClelland, Maier & neustadt

[57] ABSTRACT

A polyalkenylphenol compound represented by formula (I):

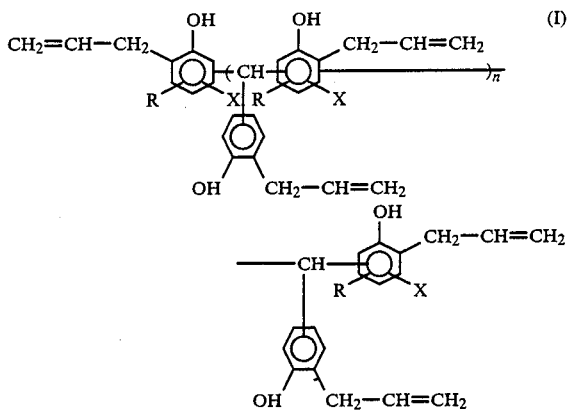

wherein R represents a hydrogen atom or a methyl group; X represents a hydrogen atom or a halogen atom; and n represents 0 or an integer of from 1 to 10. The compound is useful as a curing agent for epoxy resins or maleimide resins or a starting material for epoxy resins.

1 Claim, 2 Drawing Sheets

POLYALKENYLPHENOL COMPOUND

FIELD OF THE INVENTION

This invention relates to a novel polyalkenylphenol compound. The compound of this invention is applicable as an intermediate for epoxy resins useful for matrix resins of fiber-reinforced composite materials, heat-resistant adhesives, paints, and resist materials; a curing agent and a comonomer for maleimide resins.

BACKGROUND OF THE INVENTION

Known alkenylphenol compounds include alkenylphenols obtained from phenols and allyl chloride as disclosed in Organic Rca-Lion II, p. 27 (1949) and diallylbisphenols obtained from bisphenols as disclosed in U.S. Pat. No. 2,910,455. Also known are compositions comprising the alkenylphenols and a maleimide compound (see JP-B-55-39242, the term "JP-B" as used herein means an "examined Japanese patent publication"), compositions comprising the alkenylphenols, a maleimide compound, and an epoxy resin (see JP-A-53-134099, the term "JP-A" as used herein means an "unexamined published Japanese patent application"), and compositions comprising the alkenylphenols, a maleimide compound, and a hydrazide.

When these conventional alkenylphenols are used for crosslinking reaction, a high temperature and a long time are required for completion of the crosslinking reaction, and the resulting crosslinked product has insufficient heat resistance. It has therefore been demanded to develop a compound free from these disadvantages.

SUMMARY OF THE INVENTION

This invention provides a novel polyalkenylphenol compound represented by formula (I) shown below, which is useful as an intermediate for epoxy resins excellent in heat resistance and moldability, a curing agent, and a comonomer of maleimide resins.

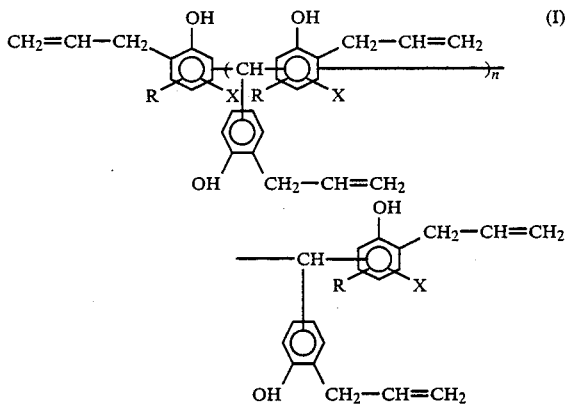

wherein R represents a hydrogen atom or a methyl group; X represents a hydrogen atom or a halogen atom; and n represents 0 or an integer of from 1 to 10. If there are two or more R or two or more X, R's or X's may be the same or different.

DETAILED DESCRIPTION OF THE INVENTION

Figure 1:
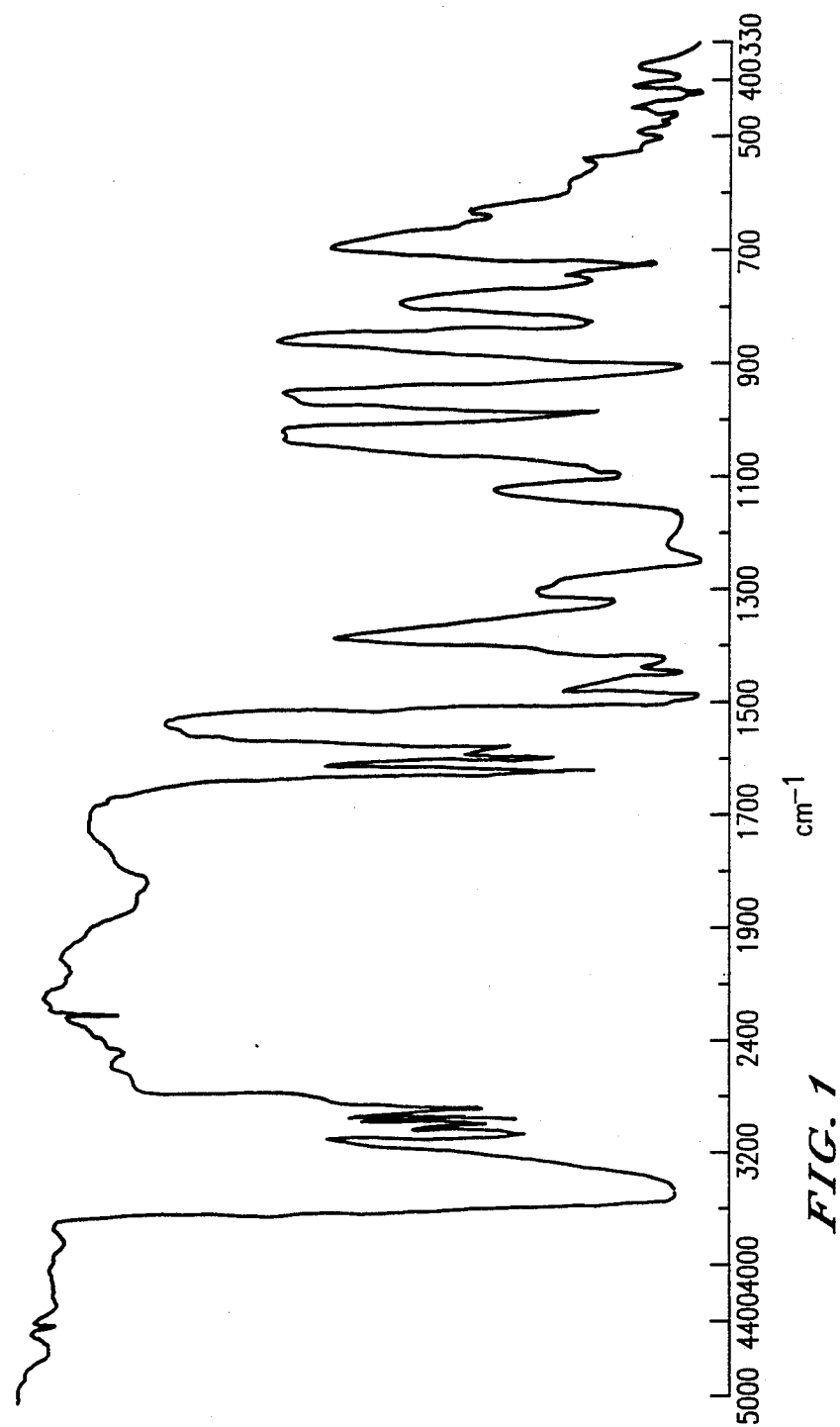
FIGS. 1 and 2 show IR and NMR spectra of the compound obtained in Example 1, respectively.

The polyalkenylphenol represented by formula (I) can be prepared by alkenylation of a specific polyphenol (precursor).

The precursor can easily be obtained by heating a phenol compound and hydroxybenzaldehyde in the presence of an acid catalyst according to the process described in JP-A-57-34122. The phenol compound is usually used in excess, e.g., in an amount of from 2 to 20 moles per mole of hydroxybenzaldehyde. The larger the excess, the smaller the molecular weight of the resulting polyphenol. The reaction is usually carried out at a temperature ranging from 80 to 180° C. for a period of from 2 to 8 hours. The higher the temperature, the shorter the reaction time. The produced water may remain in the reaction system, but continuous removal of the produced water out of the system, for example, by azeotropic distillation or distillation under reduced pressure helps progress of the reaction After completion of the reaction, the catalyst is removed, for example, by filtration, neutralization or washing with water. The excess phenol is then recovered from the reaction mixture under reduced pressure to thereby collect the polyphenol. If desired, it is possible to reduce the phenol of free form by steam distillation.

The starting phenol compound includes phenol, cresol, and bromophenol. The hydroxybenzaldehyde includes salicylaldehyde, p-hydroxybenzaldehyde, and m-hydroxybenzaldehyde. The acid catalyst to be used includes mineral acids, e.g., hydrochloric acid and sulfuric acid, organic acids, e.g., oxalic acid and p-toluenesulfonic acid, and solid catalysts, e.g., activated clay, zeolite, and ionexchange resins.

Techniques of alkenylation of phenols have hitherto been known as described, e.g., in Organic Reaction II, pp. 1-29 (1944), and they can be applied to the preparation of the polyalkenylphenol compound of the present invention. In general, a phenol compound is dissolved in an organic solvent, e.g., n-propanol, ethanol, methanol, acetone, etc., and reacted with an equimolar amount of a base, e.g., sodium hydroxide, to form a phenolate, which is then reacted with an equimole of an allyl halide, e.g., allyl chloride and allyl bromide, to effect allyl etherification. The etherification reaction is usually carried out by stirring at a temperature of from 50° to 100° C. for a period of from 1 to 10 hours. The by-produced salt is preferably removed by filtration or washing with water. This reaction proceeds substantially quantitatively. The resulting allyl ether is then subjected to Claisen rearrangement by heating at a temperature of from 100° to 250° C. to obtain an alkenylphenol in a yield of from 80 to 100%. The Claisen rearrangement can be effected in the presence or absence of a high-boiling solvent, e.g., carbitol, 2-ethoxyethanol, N,N-diethylaniline, N,N-dimethylaniline, tetraline, kerosene, paraffine oil, etc. It is known to accelerate the rearrangement reaction by addition of an inorganic salt, e.g., sodium thiosulfate and sodium carbonate. The polyalkenylphenol compound of the present invention can be synthesized in accordance with the above-described known process.

The compound according to the present invention is useful as a curing agent for epoxy resins or maleimide resins or as a starting material for epoxy resins.

(i) Curing Agent for Epoxy Resins:

A composition of an epoxy resin, the polyalkenylphenol compound of the present invention, and a curing catalyst, e.g., triarylphosphine such as triphenylphosphine, heterocyclic bases such as imidazole and benzimidazole, etc., is heated to obtain a cured product excellent in heat resistance. The resulting cured product is useful as a base of a printed circuit board, an IC sealant, a conductive paste, a paint for a resistant element, and a solder resist because of its superiority in moisture resistance, adhesiveness, and heat resistance. Upon use, the composition is dissolved in a general industrial solvent, coated on or impregnated into a substrate, and dried, followed by post-curing; or the composition is melted under heating followed by casting, or blended with a filler, e.g., silica, molybdenum disulfide, carbon, glass fibers, etc., by means of a roll, a kneader, etc. to prepare a molding powder, followed by curing by heating under pressure (ii) Curing Agent for Maleimide Resins:

A composition of a maleimide resin and the polyalkenylphenol compound of the present invention is heated to obtain a cured product excellent in heat resistance. If desired, the composition may further contain a reaction accelerator, e.g., primary, secondary or tertiary amine, quaternary ammonium compounds, heterocyclic bases, alkali metal compounds, organic peroxides, acetyl-acetonates of the transition metals, etc. The composition is excellent particularly in heat resistance and thermal expandability in low temperatures and is therefore useful as a matrix resin of carbon fiberreinforced plastic (CFRP), a base of a multilayer printed circuit board, an IC sealant, and a material for precise molding. Upon use, known molding techniques, such as autoclave molding, press molding, transfer molding, and injection molding, can be employed As a matter of course, carbon fibers, glass fibers, or other fillers (e.g., silica, carbon, fluorine resins, molybdenum disulfide, and graphite) can be used in combination.

As compared with a conventional o,o'-diallylbisphenol A, use of the polyalkenylphenol compound of the present invention as a curing agent of epoxy resins or maleimide resins results in a higher crosslinking density to thereby provide a cured product having a so much increased glass transition temperature (Tg). Accordingly, the cured product exhibits markedly improved mechanical strength in high temperatures and an improved coefficient of thermal expansion. Further, since Tg can be increased in a reduced time, reduction of a molding cycle is also expected.

The present invention is now illustrated in greater detail by way of the following Examples, but it should be understood that the present invention is not deemed to be limited thereto.

EXAMPLE 1

Synthesis of Polyphenol

In a 1 l-volume three-necked flask equipped with a thermometer, a stirrer, and a condenser were charged 470 g of phenol, 61 g of salicylaldehyde, and 0.1 g of sulfuric acid. The inner temperature was raised up to 110° C., and the reaction was continued for 4 hours. After completion of the reaction, the reaction mixture was diluted with 500 ml of methyl isobutyl ketone (MIBK) by the use of a separatory funnel and washed three times with 300 ml portions of distilled water to remove the catalyst. The residual solution was tranferred to a rotary evaporator, and MIBK and the excess phenol were removed under reduced pressure to obtain a reddish brown glassy polyphenol precursor having a melting point of 91° to 99° C.

Synthesis of Alkenylphenol

Figure 2:
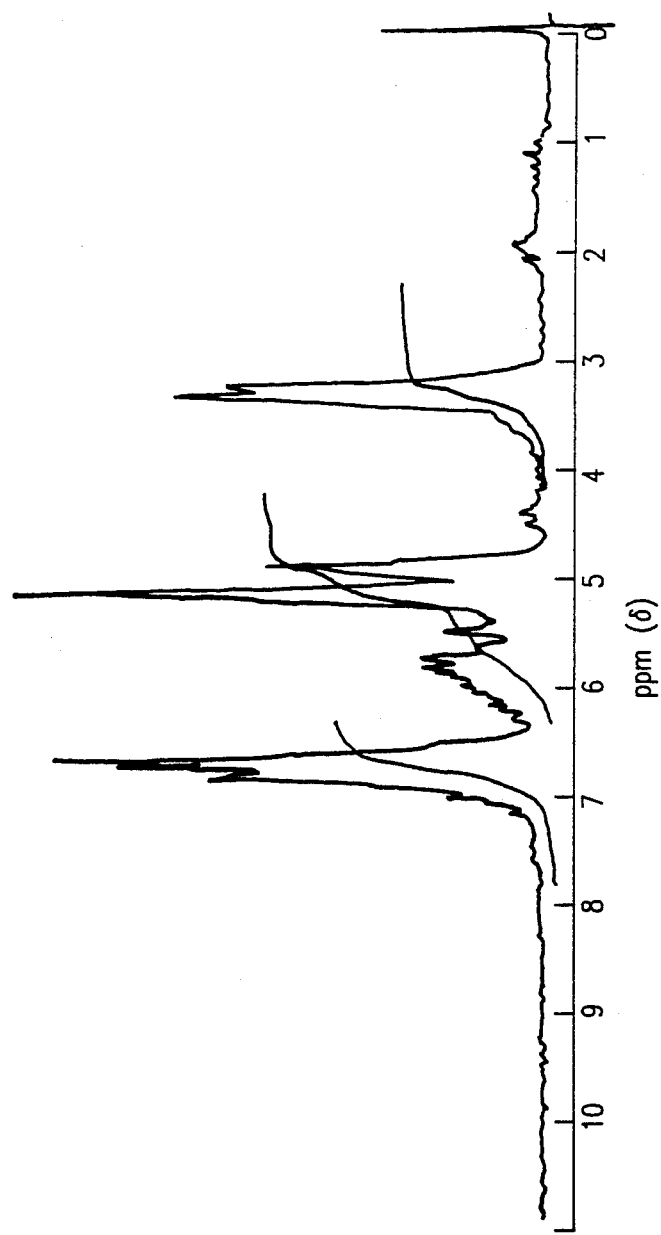

In a 1 l-volume four-necked flask equipped with a stirrer, a thermometer, a condenser, and a dropping funnel were charged 700 ml of n-propyl alcohol and 41.3 g of sodium hydroxide, and the mixture was stirred to uniformity. To the uniform mixture was added 100 g of the polyphenol precursor as prepared above, followed by stirring for 1 hour. To the reaction mixture was added dropwise 87.8 g of allyl chloride over 10 minutes, and the reaction mixture was heated to 100° C., followed by stirring for 3 hours to complete allyl etherification. The sodium chloride produced was removed by filtration, and n-propyl alcohol was recovered from the filtrate under reduced pressure. The resulting allyl ether was dissolved in 200 ml of carbitol and heated at an inner temperature of 190° to 200° C. for 6 hours to effect Claisen rearrangement The carbitol was completely removed by distillation in vacuo to obtain 141 g of a reddish brown semi-solid alkenylphenol. The IR spectrum of the product was measured by Nujol Mull method by means of JISCOA-3 infrared spectrophotometer. The NMR spectrum of the product was measuted using TMS as a standard substance in chloroform-d₃ solvent by means of JEOL JNM-PMX 60 SI NMR spectrometer. The IR and NMR spectrums are shown in FIGS. 1 and 2, respectively.

EXAMPLES 2 TO 7

Polyalkenylphenols shown in Table 1 were prepared from the corresponding starting materials in the same manner as in Example 1. The properties of the resulting compounds are also shown in Table 1.

TABLE 1

| | | | | Alkenylphenol Compound | | | | | |
|---|---|---|---|---|---|---|---|---|---|
| Example No. | Precursor (part by weight) | | | Precursor (part by weight) | Allyl Chloride (part by weight) | Yield (part by weight) | Property | Viscosity*⁴ (poise) | Avg. Mol. Wt.*⁵ |
| | Phenol | Aldehyde | Catalyst | | | | | | |
| 1 | phenol (470) | SA*¹ (61) | sulfuric acid (0.1) | 100 | 87.8 | 141 | Semi-solid | 25.6 | 413 |
| 2 | phenol (188) | SA*¹ (61) | p-toluene-sulfonic acid (0.2) | 100 | 87.8 | 144 | m.p. = 53–63° C. | — | 541 |
| 3 | phenol (188) | HBA*² (61) | ion-exchange resin*³ (3.0) | 100 | 87.8 | 140 | m.p. = 38–43° C. | — | 560 |
| 4 | phenol (470) | SA (40) HBA (21) | activated clay*³ (12.0) | 100 | 87.8 | 141 | semi-solid | 30.5 | 420 |
| 5 | cresol (540) | SA (61) | hydrochloric acid (0.1) | 100 | 68.3 | 136 | semi-solid | 32.3 | 429 |

TABLE 1-continued

| Example No. | Precursor (part by weight) | | | Alkenylphenol Compound | | | | | |
|---|---|---|---|---|---|---|---|---|---|
| | Phenol | Aldehyde | Catalyst | Precursor (part by weight) | Allyl Chloride (part by weight) | Yield (part by weight) | Property | Viscosity*4 (poise) | Avg. Mol. Wt.*5 |
| 6 | bromophenol (519) | SA (61) | hydrochloric acid (0.4) | 100 | 50.7 | 131 | m.p. = 75–81° C. | — | 673 |
| 7 | cresol (235) | SA (40) HBA (21) | hydrochloric acid (0.4) | 100 | 87.8 | 140 | m.p. = 47–54° C. | — | 503 |

Note:
*1Salicylaldehyde
*2p-Hydroxybenzaldehyde
*3Reaction temperature: 150–160° C.; The produced water was removed as a toluene azeotrope. After the reaction, the catalyst was removed by filtration.
*4Measured with an E type viscometer at 80° C.
*5Measured by gel permeation chromatography (Shodex KF-802 × 1, tetrahydrofuran, 1.0 ml/min).

While the invention has been described in detail and with reference to specific embodiments thereof, it will be apparent to one skilled in the art that various changes and modifications can be made therein without departing from the spirit and scope thereof.

What is claimed is:

1. A polyalkenylphenol compound represented by formula (I):

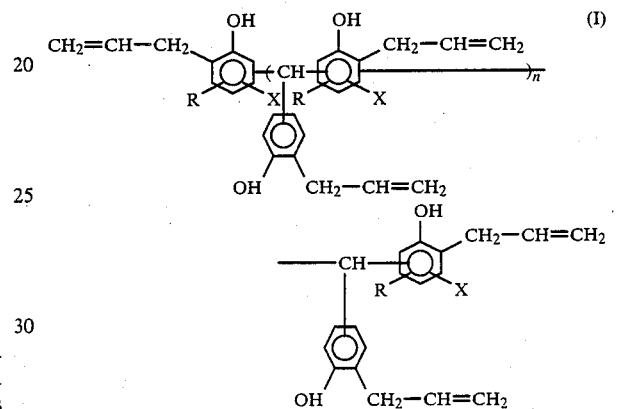

wherein R represents a hydrogen atom or a methyl group; X represents a hydrogen atom or a halogen atom; and n represents 0 or an integer of from 1 to 10.

* * * * *